United States Patent [19]

Bock

[11] Patent Number: 5,138,733
[45] Date of Patent: Aug. 18, 1992

[54] ULTRASONIC TOOTHBRUSH

[75] Inventor: Robert T. Bock, Brewster, N.Y.

[73] Assignee: Sonex International Corporation, Brewster, N.Y.

[21] Appl. No.: 674,123

[22] Filed: Mar. 25, 1991

[51] Int. Cl.⁵ .................. A61C 17/20; A61C 17/32; A46B 13/02
[52] U.S. Cl. .................................. 15/22.1; 15/167.1; 15/176.6; 318/118; 433/119; 433/216
[58] Field of Search ............... 15/22.1, 22.2, 167.1; 318/118; 433/119, 216, 118

[56] References Cited

U.S. PATENT DOCUMENTS

| 1,703,642 | 2/1929 | Sticht | 15/22.1 |
| 3,335,443 | 8/1967 | Parisi et al. | 15/22.1 |
| 3,375,820 | 4/1968 | Kuris et al. | 15/22.1 |
| 3,760,799 | 9/1973 | Crowson | 128/62 A |
| 3,809,977 | 5/1974 | Balamuth et al. | 15/22.1 |
| 3,980,906 | 9/1976 | Kuris et al. | 15/22.1 |
| 4,192,035 | 3/1980 | Kuris | 15/22.1 |
| 4,333,197 | 6/1982 | Kuris | 15/22.1 |
| 4,787,847 | 11/1988 | Martin et al. | 433/119 |

FOREIGN PATENT DOCUMENTS 3431481 2/1986 Fed. Rep. of Germany ...... 433/118

Primary Examiner—Edward L. Roberts
Attorney, Agent, or Firm—Watson, Cole, Grindle & Watson

[57] ABSTRACT

An ultrasonic toothbrush for daily removal of soft plaque including a handle constructed of a rigid material, a battery pack, an electronics driving module, a piezoelectric member, and a removable brush-head. The low voltage DC energy supplied by the battery pack is converted to an ultrasonic frequency DC current by the electronics driving module. The piezoelectric crystal resonates, expands and contracts volumetrically, in the tune with the frequency supplied by the electronics driving module and thereby converts the electronic energy into sound-wave energy. The sound-waves driving the dentifrices in the mouth of the user against the teeth causing mild cavitation within the dentifrices at the junction with the teeth, resulting in a loosening effect on the soft plaque on the surface of the teeth and in the periodontal pockets formed in the gums around the neck of the teeth. The loosened soft plaque is then dislodged by the bristle clusters of the toothbrush by the normal brushing movements of the user.

5 Claims, 2 Drawing Sheets

ULTRASONIC TOOTHBRUSH

BACKGROUND

1. Field of Invention

This invention relates to toothbrushes. More particularly the invention is concerned with an apparatus facilitating the use of ultrasonic energy to assist an otherwise manual toothbrush in loosening and removing soft plaque from the teeth of the user on a substantially daily basis.

2. Description of Prior Art

Numerous attempts has been made to develop an apparatus to remove plaque or tartar from the surface of the teeth. Some of the devices utilized sonic and/or ultrasonic energy. The devices utilizing sonic or ultrasonic energy can be grouped into three distinct categories.

One approach is the utilization of only fluids as a medium of energy transmission and plaque removal by placing an ultrasonic transducer into the middle of the mouth. This approach is impractical and physiologically dangerous due to the high energy levels it requires to be effective in absence of any mechanical scrubbing, and the uncontrolled, variable, user dependent distance between the transducer and the teeth. A typical example in U.S. Pat. No. 3,760,799.

The second approach is the application of ultrasonic energy to vibrate the toothbrush. While these teachings are aged, no application to data has demonstrated the practical feasibility of carrying out the science in this manner. The fallacy of this approach is that while the toothbrush vibrates, it absorbs the ultrasonic energy, the vibrations are dampened out by the bristles and the friction between the bristles and the tooth. Consequently, the vibrating energy is consumed before it can be effective on the surface of the teeth. An other significant drawback of some these proposals is that the toothbrush or applicator is solidly attached, otherwise fixed to the transducer, making replacement of the brush difficult and expensive, taking the device out of the economically affordable daily dental hygiene device category for the general population. Examples of these devices can be found in the following U.S. Pats.: U.S. Pat. Nos. 4,192,035 and 4,333,197 and 4,787,847.

The third and only theory reduced to practice to data is to remove hardened or calcified plaque colonies from the surface of the teeth on infrequent periodical basis. This art has been made available to professional dentists in the form of a high energy device that couples the ultrasonic energy to the teeth by a metal probe. While safe in the hands of the highly skilled and professionally trained dentists or hygienists, these devices are not suitable for daily use by the general population. Such devices could cause damage to the surface of the teeth and the surrounding tissue when utilized by un-trained novice consumers. What has occurred to data is that notwithstanding the teachings of the prior art, the ability to utilize ultrasonic energy to assist the consumer in the daily maintenance of oral hygiene in a safe and effective manner has remained unsolved.

OBJECTS AND ADVANTAGES OF THE INVENTION

Responding to the above described unsolved needs, this invention provides an ultrasonic toothbrush that is safe and effective to assist the consumer in the daily maintenance of oral hygiene. The invention attains this goal by positioning a piezoelectric transducer in the head section of an otherwise manual toothbrush. The piezoelectric crystal, resonating at or about its resonant frequency, emits ultrasonic waves between the bristles and couples the energy to the surface of the teeth via the dentifrice in the users mouth.

An object of the present invention is to provide a safe sonic of ultrasonic energy coupling mechanism to the user's teeth to dislodge and remove soft plaque.

An other object of the invention is to provide an effective cleaning device while reducing the sonic or ultrasonic energy level to the point where the daily application in the hands of an un-trained novice will not harm the surface of the teeth or the surrounding soft tissue.

A further object is to provide an inexpensive removable brush component, independent from the sealed sonic or ultrasonic energy emitter, that can be easily replaced by the consumer.

BRIEF DESCRIPTION OF THE DRAWINGS

In the accompanying drawings, in which certain modes of carrying out the present invention are shown for illustrative purposes.

DESCRIPTION OF THE PREFERRED EMBODIMENTS

Figure 1:
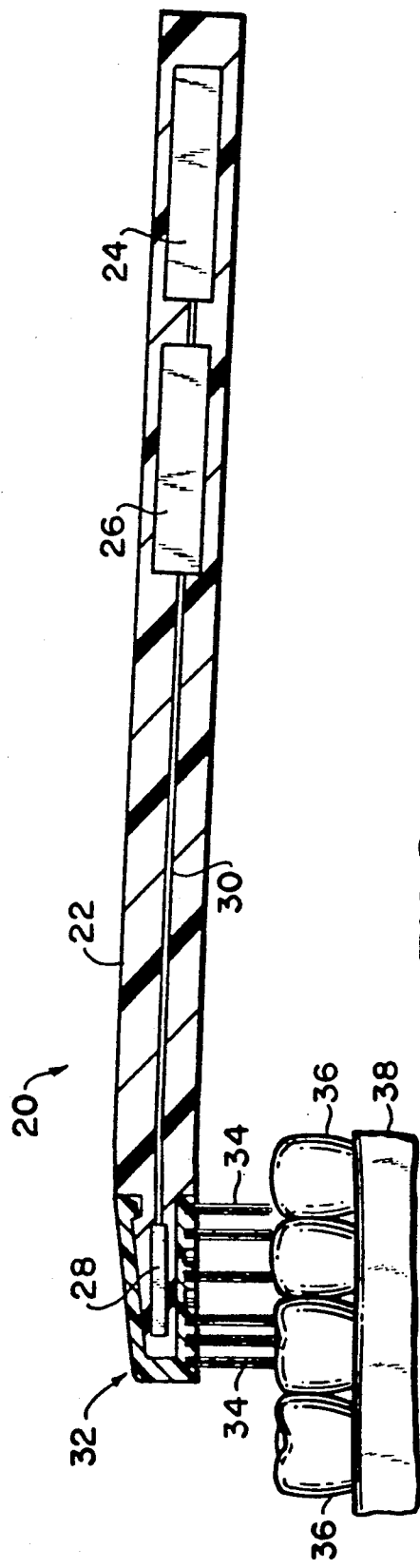
FIG. 1 shows a longitudinal cross section of the invention in the replaceable brush-head configuration, including a battery powered driving circuitry.

Referring in detail to the drawings, the reference numerals herein refer to the like numbered parts in the drawings. In the following discussion, unless otherwise qualified, the term "ultrasonic" refers to either subsonic, sonic, or ultrasonic frequencies.

An ultrasonic toothbrush 20, in accordance with the present invention, is shown in FIG. 1. The toothbrush comprises of a handle 22 constructed of a rigid material, a battery pack 24, an electronics driving module 26, a piezoelectric transducer 28, connecting wiring 30, and a removable brush-head 32 made of a flexible material that encompasses a plurality of bristle clusters 34. The toothbrush is shown in a typical cleaning position, the bristle clusters 34 in contact with the teeth 36 in the oral cavity 38. The low voltage DC energy supplied by the battery pack 24 is converted to an ultrasonic frequency DC current by the electronics driving module 26, which is connected to the piezoelectric transducer 28 by the connecting wiring 30. The piezoelectric crystal resonates, expands and contracts volumetrically, in tune with the frequency supplied by the electronics driving module 26 and thereby converts the electronic energy into sound-wave energy. The sound-waves driving the dentifrices in the mouth of the user against the teeth 36 causing mild cavitation within the dentifrices at the junction with the teeth, resulting in a loosening effect on the soft plaque on the surface of the teeth and in the periodontal pockets formed in the gums around the neck of the teeth. The loosened soft plaque is then dislodged by the bristle clusters 34 of the toothbrush 20 by the normal brushing movements of the user.

The length of the bristle clusters 34 is selected to space the transducer 28 within an effective and controlled optimum distance to the teeth, allowing the reduction of the sound energy to biologically safe levels for routine daily application without causing harm to the surface or root structure of the teeth, and the surrounding soft tissue.

Figure 3:
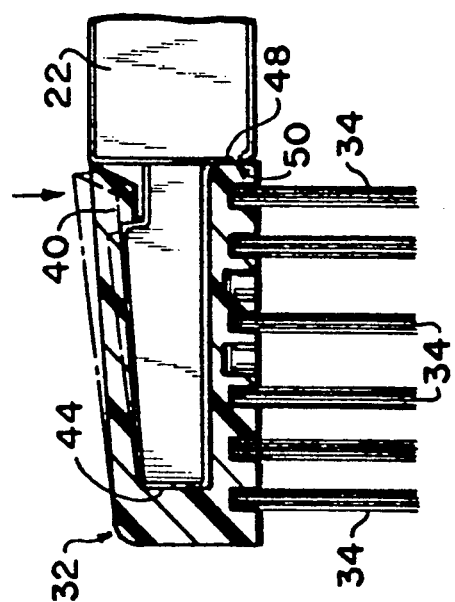
FIG. 2 and FIG. 3 shows the lock-in attachment methodology of the brush-head to the main body of the ultrasonic device, in a cross sectional view.
Figure 2:
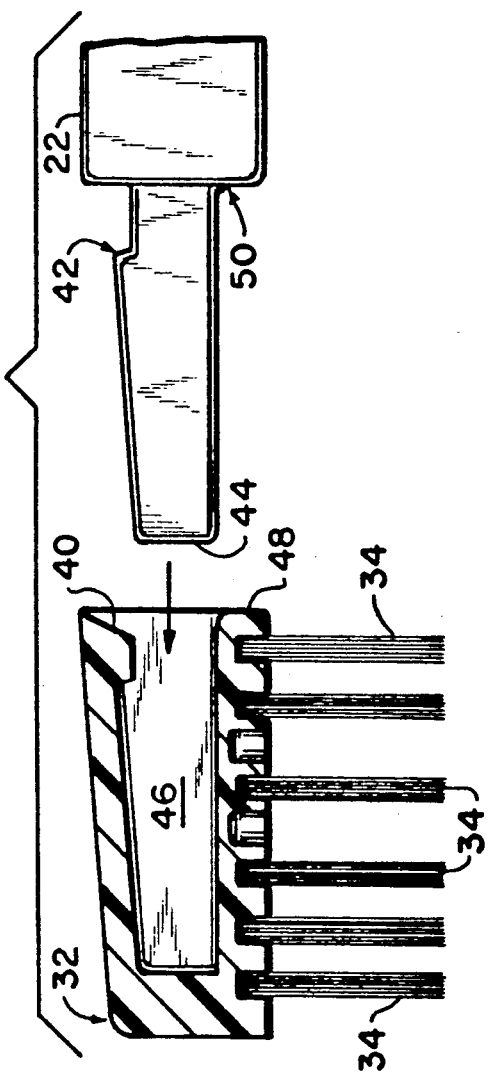

FIG. 2 and FIG. 3 illustrate the lock-in attachment methodology of the brush-head 32 to the handle 22. To achieve a firm attachment, the brush-head 32 incorporates a tapered tongue section 40 and the handle incorporates a matching groove 42. To install a replacement brush-head 32, the user engages the rigid nose 44 section of the handle 22 with the flexible mouth 46 section of the brush-head 32. Upon engagement, the user forces the brush-head 32 upon the handle 22 until the movement is stopped by the lower mating surfaces 48 and 50 of the brush-head 32 and handle 22 respectively, and the tongue 40 snaps into the groove 42.

Figure 4:
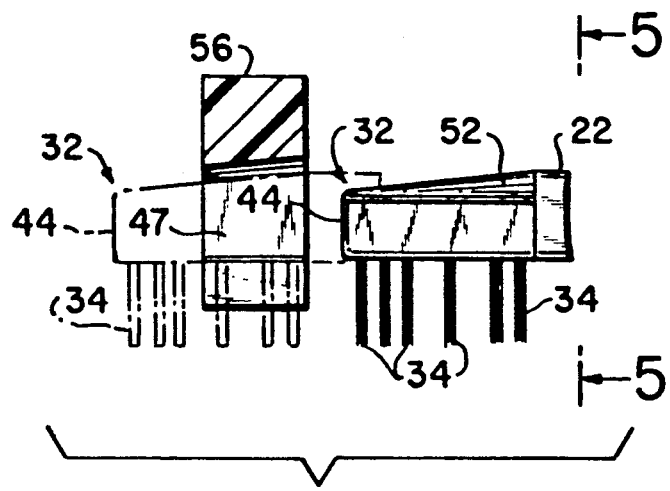
FIG. 4 and FIG. 5 and FIG. 6 shows the brush-head unlocking tool and the removal methodology of the brush-head from the main body of the device.
Figure 5:
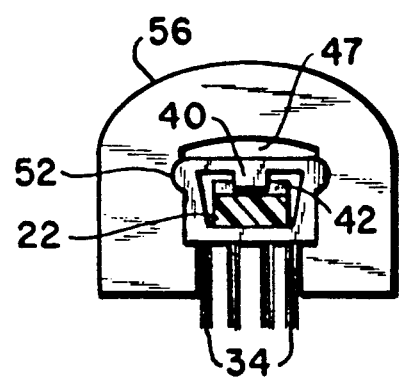
Figure 6:
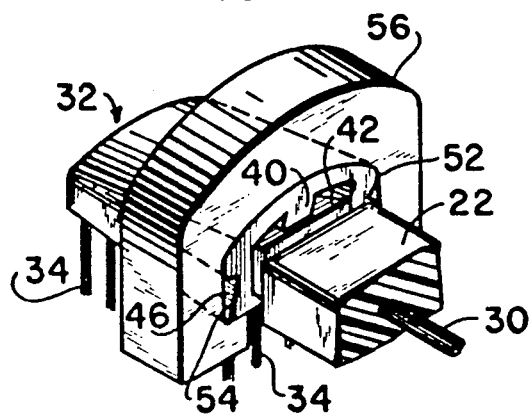

FIGS. 4, 5, and 6 illustrate the un-locking methodology of the brush-head 32 from the handle 22. The brush-head 32 incorporates a tapered abutment 52 on each side that increases in size toward its mouth 46. The internal cavity of the mouth 46 is tapered 54, and increasing the size toward the abutments 52, forming a gap between the brush-head 32 and the handle 22 adjacent to the abutments 52. A removal tool 56 constructed of a material with superior strength and rigidity to the flexible brush-head 32 material, comprises a cavity that matches the lower and straight side dimensions of the brush-head 32 but larger than the brush-head 32 in the vertical dimension. As the user slides the rigid removal tool 56 upon the flexible brush-head 32, the sides with the abutments 52 of the brush-head 32 deform inwardly, causing the top section of the brush head 32 with the tongue 40 to flex into the gap 47, out of the groove 42 of the handle 22, thereby un-locking the brush-head 32 from the handle 22.

Figure 7:
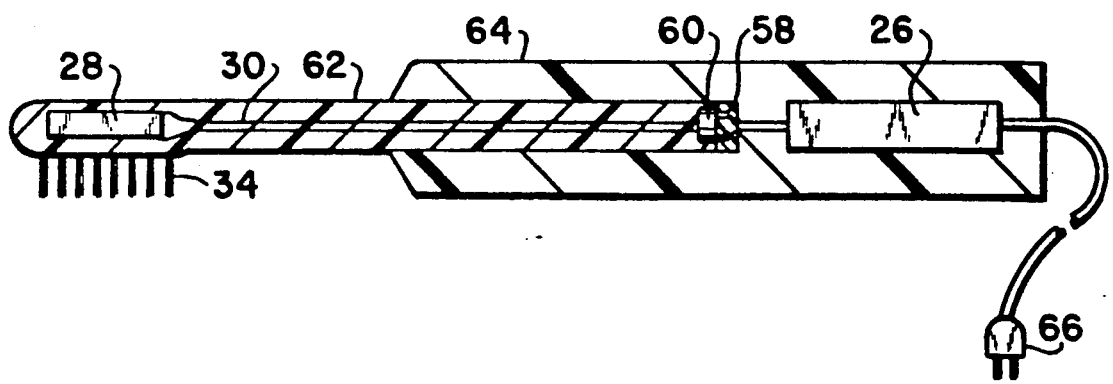
FIG. 7 shows an alternative embodiment of the invention where the replaceable brush element includes the piezoelectric crystal.

FIG. 7 shows an alternative embodiment of the invention, where the ultrasonic toothbrush 70 comprises of an AC line connector 66, a handle 64, an electronics module 26, a low voltage high frequency DC connector 58, and a replaceable brush element 62 that is further comprised of a plurality of bristle clusters 34, a piezoelectric transducer 28, connecting wiring 30, and another connector 60. The electronic module is energized by conventional AC house current through the line connector 66, The AC house current is converted to a low voltage, ultrasonic frequency DC current by the electronics module 26, which is connected to the piezoelectric transducer 28 by the connecting wiring 30 through the connectors 58 and 60. The piezoelectric crystal resonates, expands and contracts volumetrically, in tune with the frequency supplied by the electronics driving module 26 and thereby converts the electronic energy into sound-wave energy. The sound-waves driving the dentifrices in the mouth of the user against the teeth 36 causing mild cavitation within the dentifrices at the junction with the teeth, resulting in a loosening effect on the soft plaque on the surface of the teeth and in the periodontal pockets formed in the gums around the neck of the teeth. The loosened soft plaque is then dislodged by the bristle clusters 34 of the toothbrush 70 by the normal brushing movements of the user.

CONCLUSION, RAMIFICATIONS AND SCOPE OF THE INVENTION

The reader can see that the invention provides a safe and effective ultrasonic toothbrush that can be utilized by any novice in the daily maintenance of oral hygiene. The fluid coupled ultransonic energy, where metallic contact with the teeth has been eliminated, and the relatively low level but effective energy provides outstanding safety for both the teeth and the surrounding soft tissue. The reduced energy requirement is made possible by the controlled distance between the piezoelectric transducer and the teeth, that is established by the length of the bristle clusters.

While the preceding description contain many specificities, these should not be construed as limitations on the scope of the invention, but rather as an exemplification of a preferred and additional embodiments thereof. Many other variations are possible. Skilled artisans will readily be able to change dimensions, shapes and construction materials of the various components described in the embodiments and adopt the invention to all types of sonic energy applications, from subsonic through sonic to the ultrasonic range. Accordingly, the scope of the invention should be determined not by the embodiments illustrated, but by the appended claims and their legal equivalents.

I claim:
1. A dental hygiene device for use with a dentifrice, comprising:
   A. a rigid elongated member of non-conductive material having a handle end and a bristle end;
   B. a piezoelectric transducer secured to the elongated member adjacent the bristle end for contracting and expanding volumetrically in response to a changing electrical field generating vibrations of ultrasonic frequency operative to cause mild cavitation in the dentifrice to loosen soft plaque on the surface of the teeth without appreciable relative movement of the bristle end with respect to the handle end;
   C. means coupled to the piezoelectric transducer operative for generating ultrasonic frequency electrical signals and transmitting said signals to said piezoelectric transducer;
   D. A plurality of bristle clusters for carrying dentifrice and being secured to the handle of the elongated member adjacent the piezoelectric transducer, said bristle clusters to be received within the human mouth for conducting said vibrations to the dentifrice and moved across tooth and gingival surfaces for dislodging the loosened soft plaque therefrom.

2. The device of claim 1 wherein the electrical signals and vibrations are at a sonic frequency. dislodging the loosened soft plaque therefrom.

3. The device of claim 1 further comprising a removable brush holder for the bristles.

4. The device of claim 1, wherein the bristle clusters extend laterally from the elongated member opposite the piezoelectric transducer to space said transducer from the teeth.

5. A dental hygiene device for use with a dentifrice to clean teeth comprising:
   an elongated substantially rigid handle member having opposite ends in spaced apart relation;
   a removable bristle support secured to the handle near one end thereof;

a piezoelectric transducer secured within the handle adjacent the bristle support and responsive when energized for volumetrically contracting and expanding in response to a changing electrical field and generating vibrations of ultrasonic frequency in the dentifrice so as to cause mild cavitation in the dentifrice to loosen soft plaque on the surface of the teeth ;

means coupled to the piezoelectric transducer for generating ultrasonic frequency electrical signals and transmitting said signals thereto for energizing said piezoelectric transducer;

a plurality of bristle clusters for engaging the teeth surfaces and being secured to the bristle support adjacent the piezoelectric transducer and extending transversely of the support for conducting the vibrations to the dentifrice and without appreciable relative movement between the bristle clusters and the handle and dislodging the loosened plaque from the teeth.

* * * * *